(12) United States Patent
Hsu (10) Patent No.: US 8,307,466 B2
(45) Date of Patent: Nov. 13, 2012

(54) EYE PROTECTION DEVICE COMPRISING A SOFT SPONGE WITH VINYL COATING INSERT MEMBER

(76) Inventor: Roger Wen Yi Hsu, Rancho Cucamonga, CA (US)

( * ) Notice: Subject to any disclaimer, the term of this patent is extended or adjusted under 35 U.S.C. 154(b) by 514 days.

(21) Appl. No.: 12/336,224

(22) Filed: Dec. 16, 2008

(65) Prior Publication Data

US 2009/0151037 A1     Jun. 18, 2009

Related U.S. Application Data

(60) Provisional application No. 61/014,057, filed on Dec. 16, 2007.

(51) Int. Cl.
*A61F 9/02* (2006.01)

(52) U.S. Cl. .......................................................... 2/428

(58) Field of Classification Search .............. 2/428, 429, 2/430, 439, 452, 411, 9, 447
See application file for complete search history.

(56) References Cited

U.S. PATENT DOCUMENTS

| | | | | |
|---|---|---|---|---|
| 3,816,234 | A * | 6/1974 | Winfield | 428/317.9 |
| 4,397,105 | A * | 8/1983 | Richardson | 36/106 |
| 4,405,212 | A * | 9/1983 | Cooper | 351/43 |
| 5,495,303 | A * | 2/1996 | Kolentsi | 351/43 |
| 5,522,837 | A * | 6/1996 | Latina | 606/201 |
| 6,098,205 | A * | 8/2000 | Schwartz et al. | 2/428 |

* cited by examiner

*Primary Examiner* — Danny Worrell
(74) *Attorney, Agent, or Firm* — Alexander Chen, Esq.

(57) ABSTRACT

The invention discloses sponge coated with vinyl on the surface of the sponge as used in connection with eyewear for use in sports and the like; and more particularly to eyewear that utilizes inner removable sealing member, commonly referred as cup, that incorporates sponge coated with vinyl on the surface of the sponge.

17 Claims, 7 Drawing Sheets

FIG. 7

EYE PROTECTION DEVICE COMPRISING A SOFT SPONGE WITH VINYL COATING INSERT MEMBER

CROSS REFERENCE TO RELATED APPLICATION

This application claims the benefit of priority under 35 U.S.C. 119(e) to the filing date of U.S. provisional patent application No. 61/014,057 entitled "Eye protection device comprising a soft sponge with vinyl coating insert member" which was filed Dec. 16, 2007, and is incorporated herein by reference.

FIELD OF INVENTION

This present invention relates generally a sponge coated with vinyl on the surface of the sponge as used in connection with eyewear for use in sports and the like; and more particularly to eyewear utilizes inner removable sealing member, commonly referred as cup, that incorporates sponge coated with vinyl on the surface of the sponge.

BACKGROUND

Usually sports eyeglass containing an inner removable sealing member where the inner removable sealing member is designed to be attached to the back of the main eyeglass frame where the inner sealing member incorporates sponge like material to seal the space between the inner sealing member and the face of the wearer.

With respect to the use of sponge, there are several disadvantages to this typical construction. In particular, even though the sponge is air-permeable and comfortable to the wearer, it easily attracts dust and dirt, making the sponge dirty all the time. In fact, because of its air-permeable attribute, it is not able to shield the wear from the surrounding cold air. For the matter, the air-permeability also worsens the dry eye condition of the wearer.

In addition, because sponge absorbs liquids, the sponge material cannot act as floatation device. In this typical construction, the inner sealing member incorporating the typical sponge material will not float if the eyeglass assembly coupled with inner sealing member is dropped into the water by accident.

Further, because sponge absorbs liquids, the sweat of the wearer is easily absorbed. Even if the sponge is cleaned with water, the sponger will not dry easily and often the washing process will damage the glue keeps the inner sealing member attached to the sponge.

In other typical constructions, the inner sealing member has in the past incorporated Ethylene Vinyl Acetate (EVA) Plastic Materials as the material to seal the space between the inner sealing member and the face of the wearer. Nevertheless, this is undesirable because it is not comfortable to the wear in lieu of its lack of softness.

As a result, it is desired that a material that is sponge like in its softness but is not air-permeable is available for the use in the context of sports eyewear. Specifically, it is left to desire an eyewear that utilizes inner removable sealing member, commonly referred as cup, where the inner removable sealing member further incorporates sponge coated with vinyl on the surface of the sponge.

SUMMARY DESCRIPTION

The invention discloses a sport eyeglasses assembly which includes an eyeglasses frame having a bridge element, at least one lens, a left frame part and a right frame part, wherein each of said frame parts comprises lens retaining portion, a layer of sponge coated vinyl material, wherein said sponge coated vinyl material is attached to the rear of said eyeglasses frame. In addition, the sponge coated vinyl material is attached to the rear of said eyeglasses frame by the use of glue, fasteners, and clips. Here the sponge coated vinyl material will not absorb liquid and is not air permeable.

In addition, inner sealing member further comprises a plurality of struts positioned to the rear of said eyeglasses frame; wherein said vinyl coated sponge material further comprises a plurality of holes; wherein said plurality of struts fit said plurality of holes. Typically the struts are constructed in a T shape configuration and made of silicon gel material. The struts are attached to the eyeglasses frame by the use of fasteners, and or glue.

In another embodiment, a sport eyeglasses assembly is disclosed which comprise an eyeglasses frame having a bridge element, at least one lens, a left frame part and a right frame part, wherein each of said frame parts comprises lens retaining portion; an inner sealing member, wherein the inner sealing member comprising a bridge element, a left frame part and a right frame part, and a layer of sponge coated vinyl material, wherein said sponge coated vinyl material is attached to the rear of said inner sealing member. The sponge coated vinyl material is attached to the rear of said inner sealing member by the use of glue or fasteners and clips. In this construction the sponge coated vinyl material will not absorb liquid and is not air permeable. In addition, the inner sealing member further comprises at least one lens.

In a preferred embodiment, the inner sealing member further comprises a plurality of struts positioned to the rear of said inner sealing member; wherein said vinyl coated sponge material further comprises a plurality of holes, wherein said plurality of struts fit the plurality of holes. In yet another preferred embodiment, the struts are constructed in a T-shape configuration. Typically, the struts are made of silicon gel material. In yet a further preferred embodiment, the struts are attached to the inner sealing member by the use of fasteners or the use of glue.

DETAILED DESCRIPTION

An eye shielding system is provided that permits a non air-permeable inner removable sealing member to be releasably secured to the frame of the eyeglasses or goggles. An inner removable sealing member is provided that encloses the area between the face and the frame. The eyeglasses or goggles retain lenses and an inner removable sealing member to prevent debris or contaminants from reaching the eyes, and have a frame, and temple connectors. The frame provides support for the inner removable sealing member. The forward part of the inner removable sealing member is fitted to the rear side of the frame, and is reversibly retained thereby. The inner removable sealing member extends rearwardly and seals with the face of the wearer with the use of sponge coated with vinyl.

The sponge coated with vinyl which will prevent air from passing through the sponge and therefore resists passage of sprayed liquids or solids and further prevents airborne liquid or solid debris or contaminants from reaching the face and into contact with the eyes.

This present invention relates generally to sponge coated with vinyl on the surface of the sponge as used in connection with eyewear for use in sports and the like; and more particularly to eyewear that utilizes inner removable sealing member, commonly referred as cup, that incorporates sponge coated with vinyl on the surface of the sponge.

In one embodiment, the eyewear utilizes inner removable sealing member, commonly referred as a cup, where it incorporates sponge coated with vinyl on the surface of the sponge to seal the space between the inner sealing member and the face of the wearer. Specifically, the sponge coated with vinyl on the surface of the sponge is attached to the back of the inner sealing member by the use of glue, clips, fasteners, or the like methods.

Typically, the sponge can be coated with vinyl either by spraying vinyl to the surface of the sponge. In addition, where vinyl can be maintained in a state of liquid, the sponge can be coated with vinyl by dipping the sponge into the liquid vinyl.

Depending on the necessity, vinyl can be coated on one, two, three or four sides of the sponge. In effect, the sponge coated with vinyl on the surface of the sponge will float on the water. It will not absorb liquid and is not air permeable.

In another embodiment, the sponge coated with vinyl on the surface of the sponge can be attached directly to the back of the eyewear main frame without the use of the inner sealing member. In this embodiment, the sponge coated with vinyl on the surface of the sponge is attached to the back of the eyewear main frame by glue, clips, fasteners or the like methods.

In yet another embodiment, the inner removable sealing member that incorporates sponge coated with vinyl on the surface of the sponge to seal the space between the inner sealing member and the face of the wearer additionally contain lenses on the removable sealing member.

In one other embodiment, the inner sealing member incorporates sponge coated with vinyl on the surface of the sponge where the inner sealing member additionally incorporates T shape struts made with soft gel like material such as gelatin to support the shape of the sponge. This T shape struts are provided because the sponge as used to seal the space between the inner sealing member and the face tends to loose it shape and collapses as a result of extensive use. In this embodiment, the T shape struts are attached to the inner sealing member by either screws, clues, or the like methods. Matching T shape holes are provided in the sponge coated with vinyl on the surface of the sponge. The sponge coated with vinyl on the surface of the sponge is then attached to the rear of the inner sealing member by glue, clips, fasteners, or the like methods where the matching T shape holes fits the matching T shape struts tightly.

Figure 1:
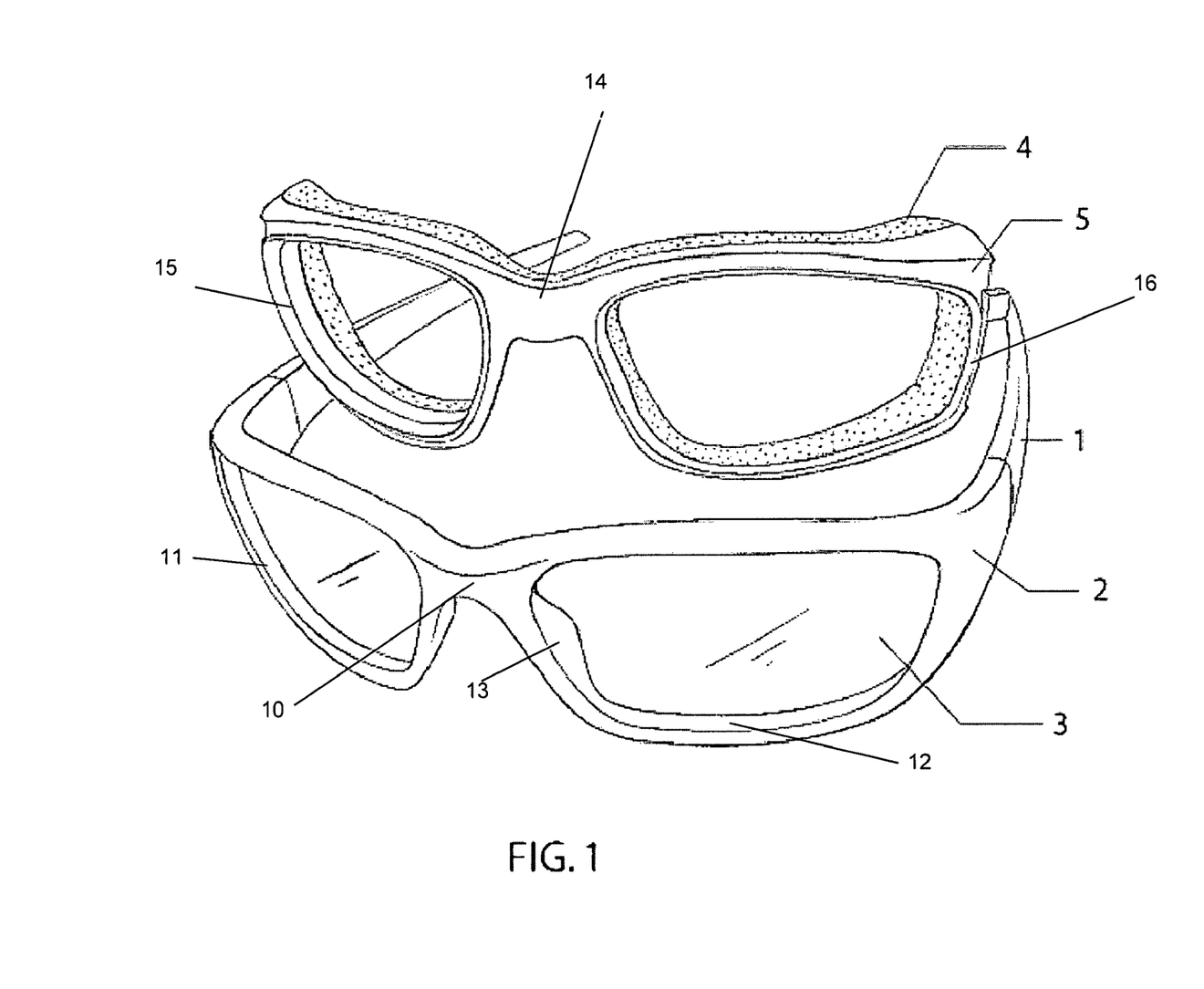
FIG. 1 is a perspective view of the eyeglass of present invention wherein the inner sealing member incorporates sponge coated with vinyl as it is attached to the rear of the inner sealing member.

As shown in FIG. 1, eyeglass of present invention is depicted, which includes a main eyeglass frame 2 having a left frame part 11 and a right frame part 12, each frame parts having a lens retaining portion 13, and a bridge element 10, lenses 3 on the main eyeglass frame 2, and temple 1. FIG. 1 also depicts the inner sealing member 5 having a left frame part 15, a right frame part 16, and a bridge element 14 wherein the inner sealing member incorporates sponge coated with vinyl 4 as it is attached to the rear of the inner sealing member 5.

Figure 2:
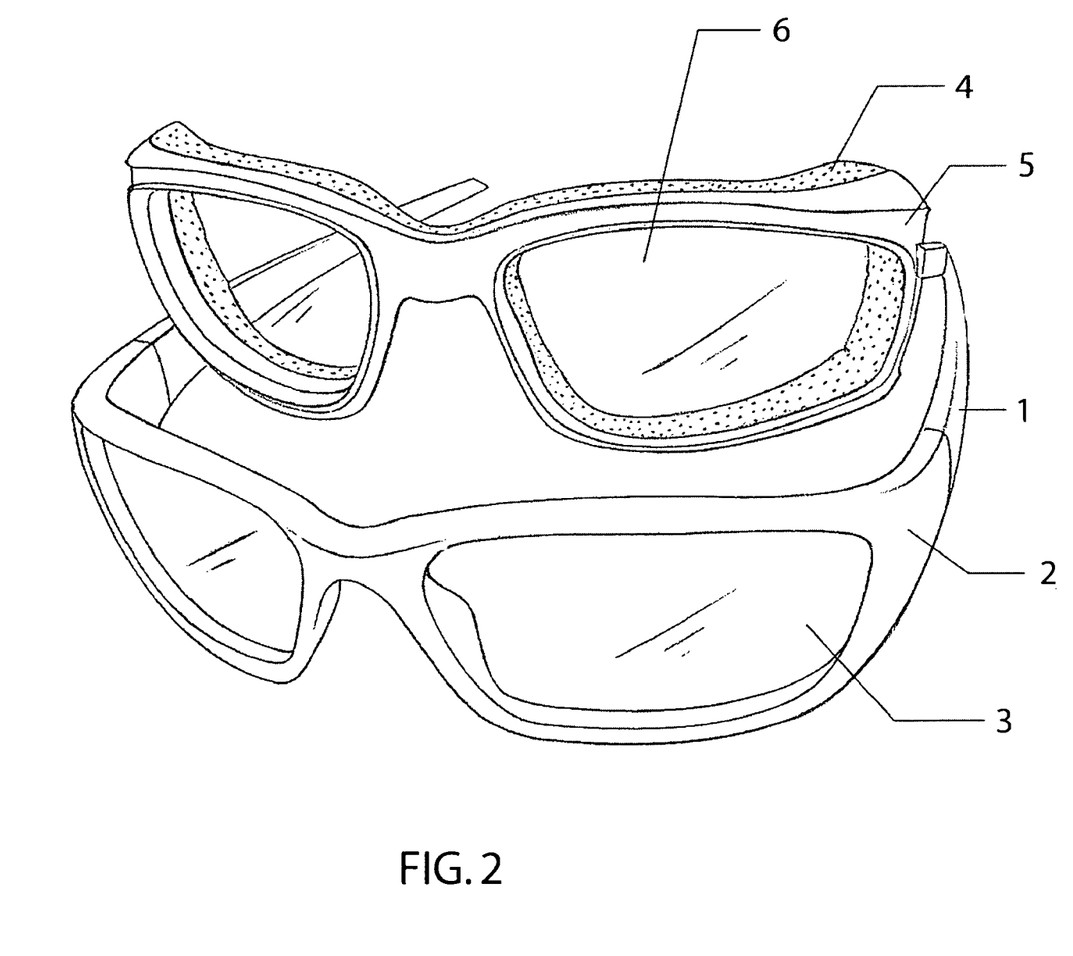
FIG. 2 is another depiction of the present invention where the main eyeglass frame where the inner sealing member further contains lenses on inner sealing member.

FIG. 2 is another depiction of the present invention where the main eyeglass frame 2, lenses 3, temple 1 and an inner sealing member 5. FIG. 1 depicts the inner sealing member 5 incorporating sponge coated with vinyl 4 as it is attached to the rear of the inner sealing member 5 where the inner sealing member 5 further contains lenses 6 on inner sealing member.

Figure 3:
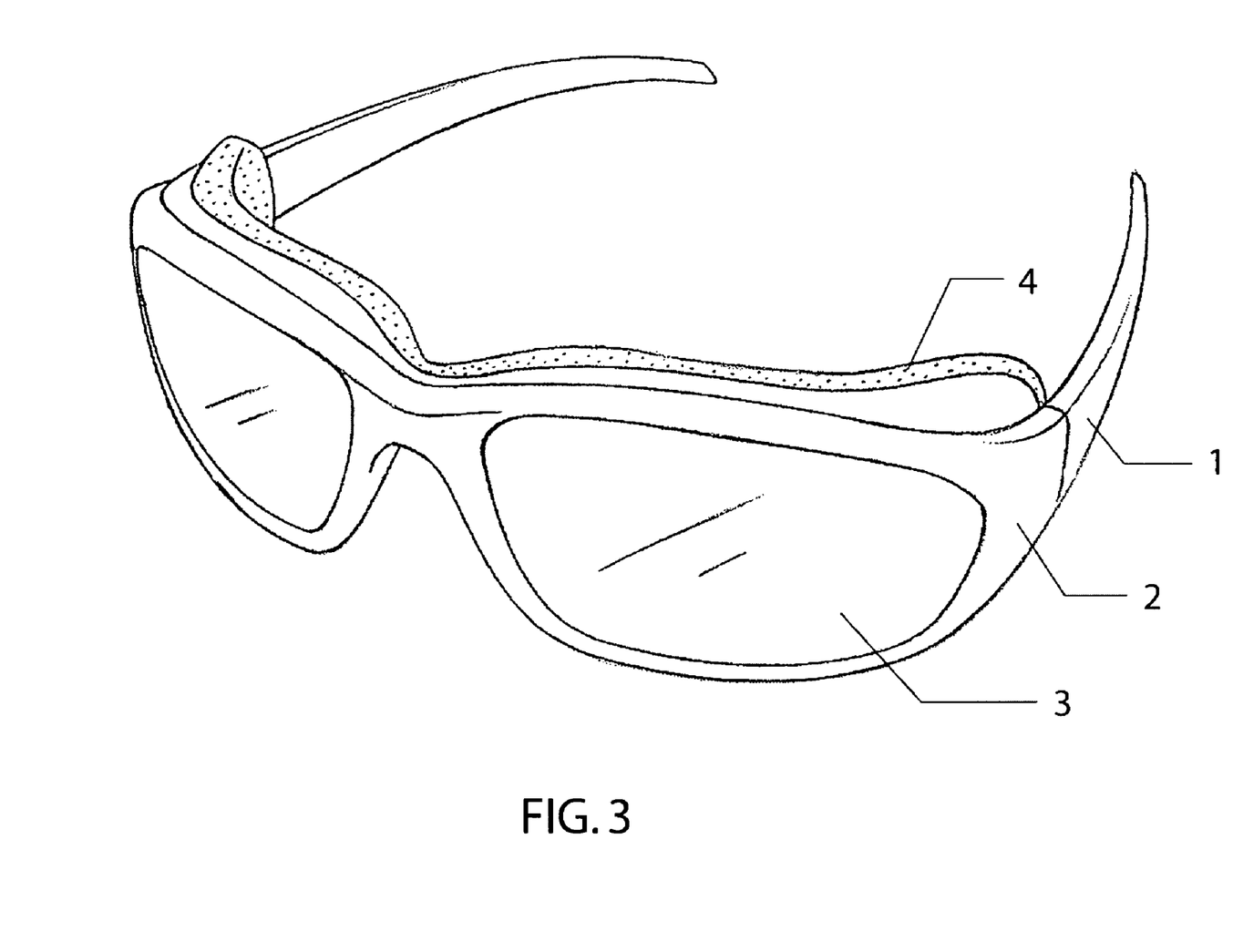
FIG. 3 depicts the sponge coated with vinyl can be attached directly to the back of the main eyeglass frame without the inner sealing member.

As shown in FIG. 3, in this depiction, the sponge coated with vinyl 4 can be attached directly to the back of the main eyeglass frame 2 without the inner sealing member.

Figure 4:
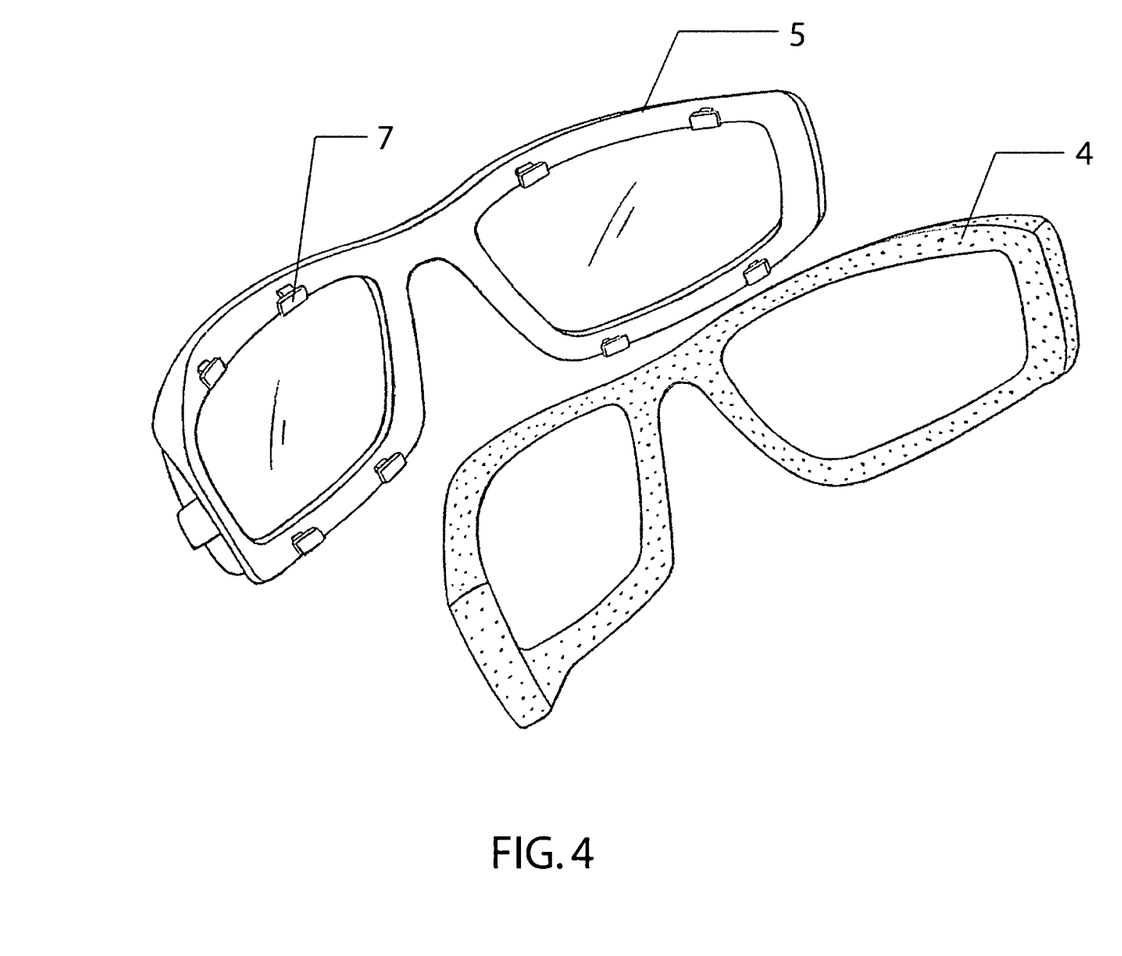
FIG. 4 is another depicts sponge coated with vinyl as before it is attached to the rear of the inner sealing member.

FIG. 4 is another depiction of the present invention. The inner sealing member 5 is depicted as it incorporates soft gel struts 7 to support the shape of the sponge. The soft gel struts 7 are attached to the inner sealing member by screws, glue, clips or the like methods. Also depicted is the sponge the sponge coated with vinyl 4 as before it is attached to the rear of the inner sealing member 5.

Figure 5:
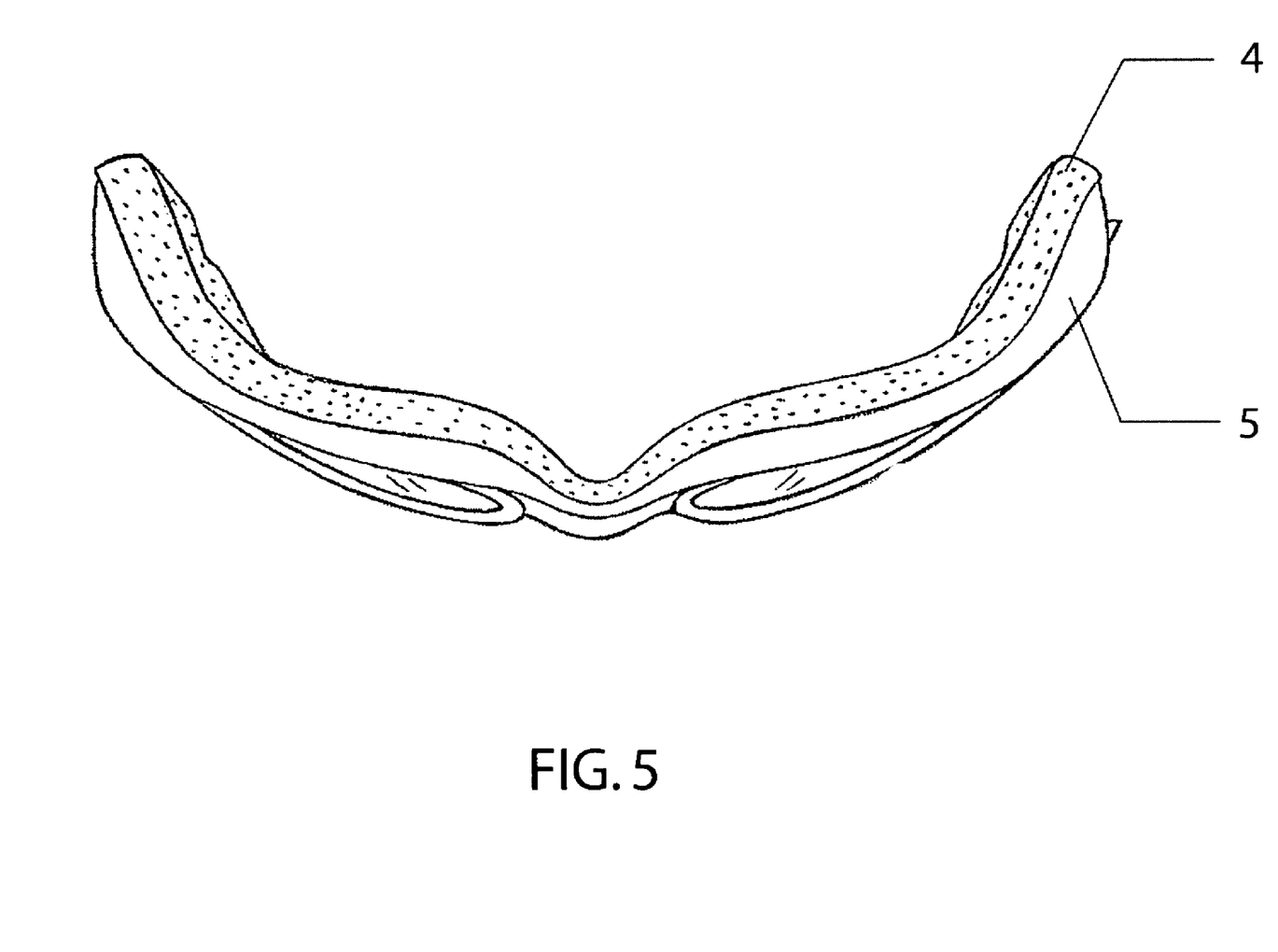
FIG. 5 depicts from the top where sponge coated with vinyl is attached to the back of the inner sealing member.

FIG. 5 is another depiction of the present invention. The view depicts from the top where sponge coated with vinyl 4 is attached to the back of the inner sealing member 5.

Figure 6:
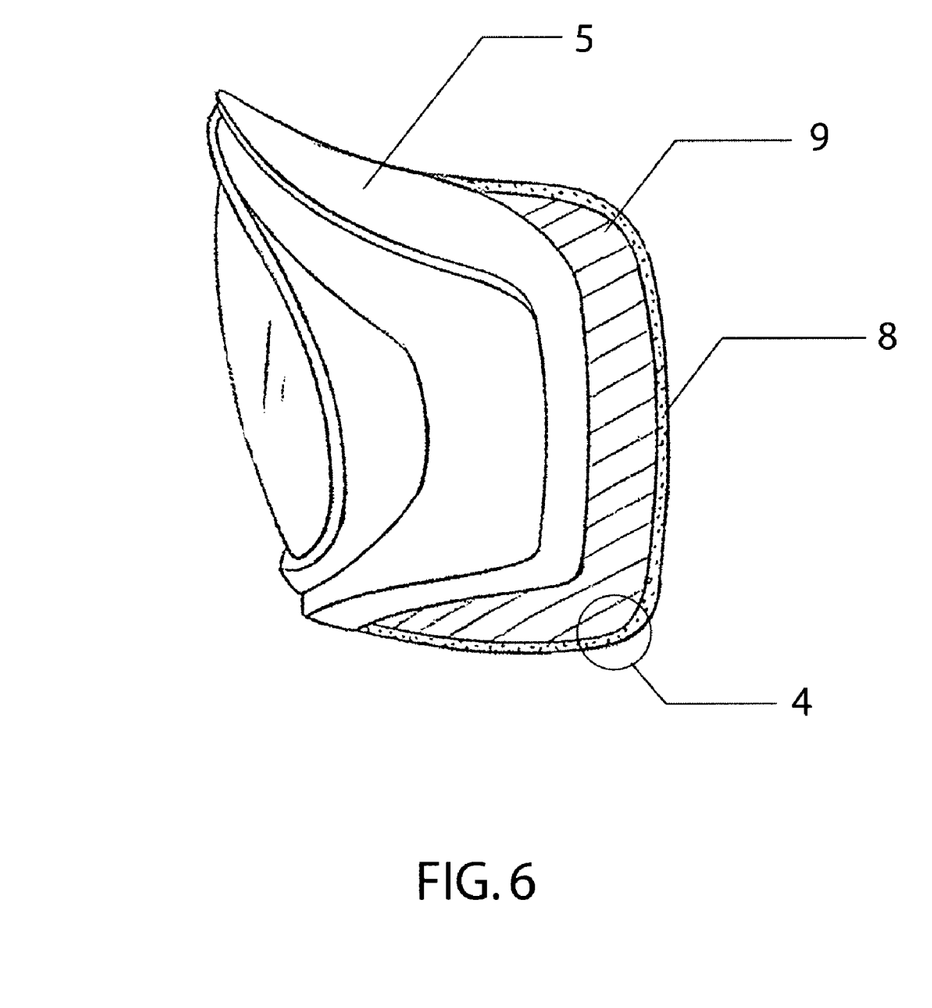
FIG. 6 depicts the side view of an inner sealing member as attached to the sponge coated with vinyl.

FIG. 6 depicts the side view of an inner sealing member 5 as attached to the sponge coated with vinyl 4. Here the figure further depicts the cross section view of the sponge coated with vinyl 4 where the sponge 9 is depicted as being coated with a layer of vinyl 8 on the surface of the sponge 9.

Figure 7:
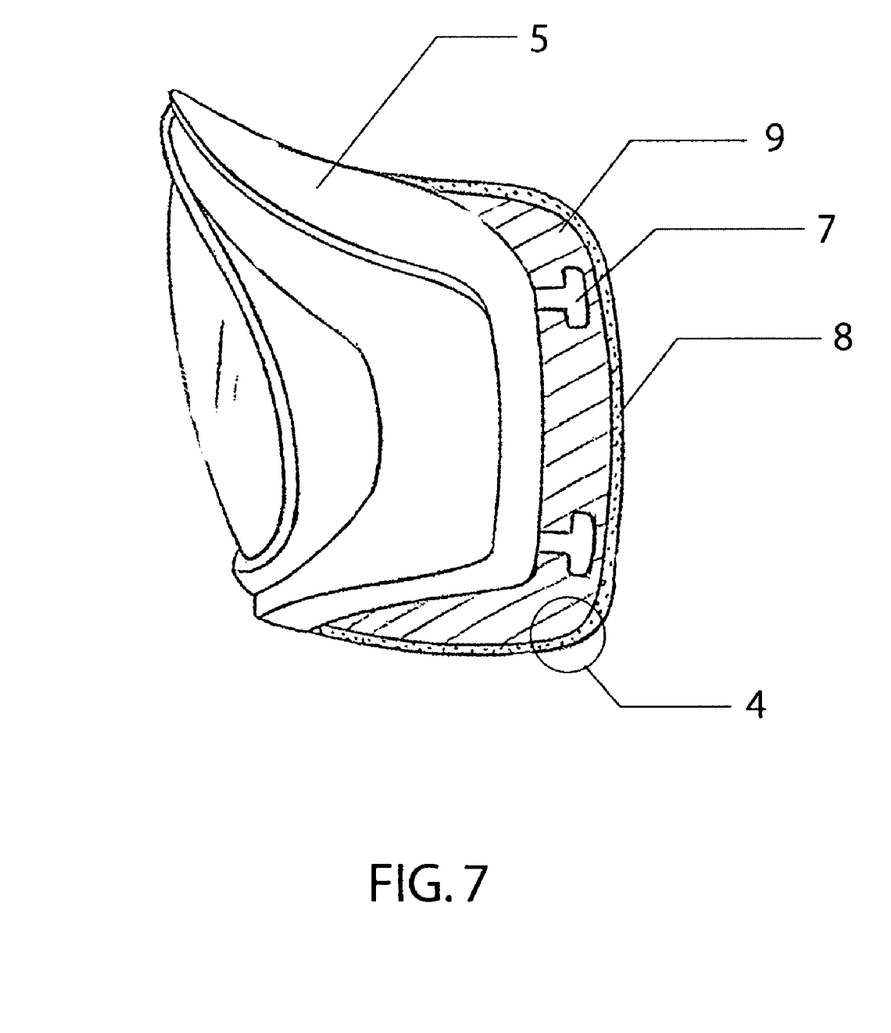
FIG. 7 depicts the side view of an inner sealing member as attached to the sponge coated with vinyl further depicting the cross section view of the sponge coated with vinyl.

FIG. 7 depicts the side view of an inner sealing member 5 as attached to the sponge coated with vinyl 4. Here the figure further depicts the cross section view of the sponge coated with vinyl 4 where the sponge 9 is depicted as being coated with a layer of vinyl 8 on the surface of the sponge 9. Here, the figure further depicts the inner sealing member 5 incorporating the soft gel struts 7 to support the form of the sponge coated with vinyl 4.

What is claimed is:

1. A sport eyeglasses assembly, comprising: a sport eyeglasses frame having a bridge element, at least one lens, a left frame part and a right frame part, wherein each frame part is angled to taper to a curvature of a face of a wearer, wherein each of said frame parts comprises lens retaining portion, a layer of vinyl coated sponge material, wherein said vinyl coated sponge material is attached to the rear of said eyeglasses frame wherein a plurality of struts are positioned to the rear of said eyeglasses frame; wherein said vinyl coated sponge material further comprises a plurality of holes; wherein said plurality of struts fit said plurality of holes; wherein said struts are constructed in a T shape configuration; wherein said struts supports the form of said vinyl coated sponge material; wherein said struts are made of silicon gel material.

2. The sport eyeglasses assembly of claim 1 wherein said vinyl coated sponge material is attached to the rear of said eyeglasses frame by the use of glue.

3. The sport eyeglasses assembly of claim 1 wherein said vinyl coated sponge material is attached to the rear of said eyeglasses frame by the use of fasteners.

4. The sport eyeglasses assembly of claim 1 wherein said vinyl coated sponge material is attached to the rear of said eyeglasses frame by the use of clips.

5. The sport eyeglasses assembly of claim 1 wherein said vinyl coated sponge material will not absorb liquid.

6. The sport eyeglasses assembly of claim 1 wherein said vinyl coated sponge material is not air permeable.

7. The sport eyeglasses assembly of claim 1 wherein said struts are attached to the eyeglasses frame by the use of fasteners.

8. The sport eyeglasses assembly of claim 1 wherein said struts are attached to the eyeglasses frame by the use of glue.

9. A sport eyeglasses assembly, comprising: an eyeglasses frame having a bridge element, at least one lens, a left frame part and a right frame part, wherein each frame part is angled to taper to a curvature of a face of a wearer, wherein each of said frame parts comprises lens retaining portion; an inner sealing member, wherein the inner sealing member comprising a bridge element, a left frame part and a right frame part, and a layer of vinyl coated sponge material, wherein said vinyl coated sponge material is attached to the rear of said inner sealing member wherein a plurality of struts are positioned to the rear of said inner sealing member; wherein said vinyl coated sponge material further comprises a plurality of holes; wherein said plurality of struts fit said plurality of holes; wherein said struts are constructed in a T shape configuration; wherein said struts supports the form of said vinyl coated sponge material; wherein said struts are made of silicon gel material.

10. The sport eyeglasses assembly of claim 9 wherein the vinyl coated sponge is attached to the rear of said inner sealing member by the use of glue.

11. The sport eyeglasses assembly of claim 9 wherein the vinyl coated sponge material is attached to the rear of said inner sealing member by the use of fasteners.

12. The sport eyeglasses assembly of claim 9 wherein the vinyl coated sponge material is attached to the rear of said inner sealing member by the use of clips.

13. The sport eyeglasses assembly of claim 9 wherein the vinyl coated sponge material will not absorb liquid.

14. The sport eyeglasses assembly of claim 9 wherein the vinyl coated sponge material is not air permeable.

15. The sport eyeglasses assembly of claim 9 wherein said inner sealing member further comprises at least one lens.

16. The sport eyeglasses assembly of claim 9 wherein said struts are attached to the inner sealing member by the use of fasteners.

17. The sport eyeglasses assembly of claim 9 wherein said struts are attached to the inner sealing member by the use of glue.

* * * * *